US005728905A

United States Patent [19]
Clegg et al.

[11] Patent Number: 5,728,905
[45] Date of Patent: Mar. 17, 1998

[54] VINYL CHLORIDE PRODUCTION PROCESS

[75] Inventors: Ian Michael Clegg, Middlewich; Ray Hardman, Chester, both of United Kingdom

[73] Assignee: EVC Technology AG, Zug, Switzerland

[21] Appl. No.: 433,384

[22] PCT Filed: Sep. 7, 1994

[86] PCT No.: PCT/GB94/01944

§ 371 Date: Aug. 15, 1995

§ 102(e) Date: Aug. 15, 1995

[87] PCT Pub. No.: WO95/07251

PCT Pub. Date: Mar. 16, 1995

[30] Foreign Application Priority Data

Sep. 7, 1993 [GB] United Kingdom ............ 9318507

[51] Int. Cl.$^6$ .................................. C07C 17/15
[52] U.S. Cl. ........................................ 570/224
[58] Field of Search ................................. 570/224

[56] References Cited

U.S. PATENT DOCUMENTS

| | | | |
|---|---|---|---|
| 3,551,506 | 12/1970 | Weinstein | 570/224 |
| 3,629,354 | 12/1971 | Beard | 570/224 |
| 4,100,211 | 7/1978 | Magistro | 570/224 |
| 5,097,083 | 3/1992 | Stauffer | 570/224 |

FOREIGN PATENT DOCUMENTS

| | | | |
|---|---|---|---|
| 2285359 | 4/1976 | France. | |
| 1039369 | 8/1966 | United Kingdom | 570/224 |
| 1492945 | 11/1977 | United Kingdom. | |
| 2101596 | 1/1983 | United Kingdom. | |
| WO 95/07249 | 3/1995 | WIPO. | |
| WO 95/07250 | 3/1995 | WIPO. | |

*Primary Examiner*—C. Warren Ivy
*Assistant Examiner*—Lyman H. Smith
*Attorney, Agent, or Firm*—Woodcock Washburn Kurtz Mackiewicz & Norris LLP

[57] ABSTRACT

A method for the production of vinyl chloride monomer by catalytic oxychlorination of ethane wherein HCl is supplied in excess of the stiochiometric requirement for chlorine in the reaction.

4 Claims, No Drawings

VINYL CHLORIDE PRODUCTION PROCESS

This case is a 35 USC 371 National stage filing of PCT/G894/01944, published as WO95/07251 on Mar. 16, 1995.

The present invention relates to a process for the production of vinyl chloride monomer (VCM) from ethane via oxychlorination of ethane. More particularly, the invention relates to a method for controlling the selectivity of the oxychlorination of ethane.

VCM is most commonly produced from ethylene and chlorine feeds by chlorinating ethylene to produce 1,2-dichloroethane and subsequently dehydrochlorinating this intermediate to yield VCM.

The cost of ethylene is a significant contribution to the final cost of VCM produced by this method. Accordingly, interest has been shown in alternative hydrocarbon feeds in VCM production.

A prime candidate for an alternative hydrocarbon from which VCM may be produced is ethane. Not only is ethane cheaper than ethylene, but the chemistry of its conversion to VCM has distinct advantages. For example, the favoured oxychlorination reaction is a single step process in which ethane can be directly converted to VCM:

$$C_2H_6 + Cl + O_2 \rightarrow C_2H_3Cl + \text{other products} + H_2O$$

The chlorine source may be provided in the form of $Cl_2$ gas, hydrogen chloride or a chlorinated hydrocarbon.

The selectivity of this reaction to VCM in favour of the "other products" is not total and is a source of inefficiency in the oxychlorination process. Other products may include recyclable intermediates such as ethylene and 1,2-dichloroethane, which may ultimately be converted to VCM. However, an appreciable percentage of these other products comprises burning products (mainly $CO_2$) which result from oxidation of ethane in an uncontrolled manner.

Such products cannot be economically recycled in the VCM production process and represent wastage of raw material.

The selectivity of the oxychlorination reaction towards VCM and, most importantly, away from the burning products may be improved in a number of ways. A number of catalysts have been proposed in the art which affect the selectivity of the oxychlorination reaction. For example, GB 1492945 (BP) discloses the use of a Copper/Potassium/Cerium catalyst for the oxychlorination of ethane. However, the product spectrum quoted in the results is incomplete, with up to 18% of the ethane feed unaccounted for. Furthermore, the ethane feed is diluted with Nitrogen to an impractical degree.

In our copending United Kingdom Patent Application No. 9318501.5, filed contemporaneously herewith, we disclose a novel catalyst for catalysation of the oxychlorination reaction. A full spectrum of by-products is given in the examples of this application.

We have now developed a new and different technique for the reduction of the amount of burning products generated during the oxychlorination reaction. The technique may be used in any oxychlorination process, for example that described in our copending United Kingdom Patent Application No. 9318497.6, filed contemporaneously herewith, in conjunction with any catalyst.

According to a first aspect of the present invention, there is provided a method for the production of VCM by catalytic oxychlorination of ethane wherein HCl is supplied in excess of the stoichiometric requirement for chlorine in the reaction.

The HCl may be the only source of chlorine in the oxychlorination reaction. Alternatively, it may be supplied together with a second chlorine source, such as a chlorinated hydrocarbon or chlorine itself. All the chlorine requirement may be supplied by the second chlorine source.

In general, the greater the excess of HCl supplied over its stoichiometric requirement the greater the beneficial effect on the selectivity of the oxychlorination reaction. Where there is no requirement for HCl, because all the chlorine requirement is supplied in an alternative form, any quantity of HCl which is added will have a beneficial effect.

The ratio of HCl to ethane used in the reaction is preferably in the range 0.1 to 10 on a molar basis, and advantageously in the range 0.5 to 3.

Because not all the HCl is consumed in the reaction, HCl will leave the reactor together with the products of the reaction. Preferably, the excess HCl is recycled to the reactor.

Recovery of the HCl in order to recycle it may be accomplished by any conventional means known in the art.

According to a second aspect of the present invention, there is provided the use of HCl in excess of its stoichiometric requirement for the enhancement of the selectivity of the catalytic oxychlorination of ethane in the production of VCM.

The invention may be used in any catalytic oxychlorination process.

Preferably, the catalyst used in conjunction with the invention is a copper-based catalyst. Advantageously, this catalyst may further comprise an alkali metal and a lanthanide element, such as Potassium and Cerium respectively.

A preferred catalyst is described in our copending United Kingdom Patent Application No. G12134P, filed contemporaneously herewith.

The reaction conditions employed may be any suitable conditions known in the art. Preferred conditions are set out in our copending United Kingdom Patent Application No. G12468P, filed contemporaneously herewith.

The invention will now be described for the purposes of illustration only with reference to the following examples.

EXAMPLE 1

A catalyst containing 1.3% copper and 3.4% potassium was prepared by evaporation of an aqueous solution of the metal chlorides onto an Alumina carrier. To a 250 cm$^3$ sample of de-ionised water was added 20 g of $CuCl_2.2H_2O$ and 35g of KCl. The resultant solution was added stepwise to 500 g of catalyst carrier (Type SAHT-99, Production Chemicals Ltd.). This catalyst paste was dried by heating to 120° C. for 24 hours and then sieved to break up agglomerates before use. When prepared, the catalyst was found to have a surface area of 1 m$^2$/g and to have a mean particle size of 90 microns.

A catalyst charge of 400 cm$^3$ was loaded into a 50.8 mm diameter Inconel fluidised bed reactor to give a bed length of approximately 40 cm. The conversions and selectivity achieved by the catalyst was measured using an on-line gas chromatograph. The reactor was heated electrically to the desired operating temperature and a reactor feed consisting of ethane, hydrogen chloride, nitrogen and oxygen was used. The feed details together with the results are shown as example 1, table 1.

EXAMPLE 2

Using the same catalyst as example 1 the reactor was operated under the same conditions except with an increased hydrogen chloride flow and without a nitrogen flow. The results are displayed in table 2.

In example 2, the excess hydrogen chloride supplied was not able to take part in the oxychlorination reaction as all of the oxygen has been consumed at the lower hydrogen chloride flow rate shown in example 1. It is seen from the table that by increasing the flow of hydrogen chloride to the reactor, the yield to burning products (mainly $CO_2$) decreases from 8.44 to 7.27% of the ethane reacted.

EXAMPLE 3

Using a catalyst of the same composition as that in example 1 and utilising a mixed chlorohydrocarbon feed, the effect of increasing the hydrogen chloride flow is shown as example 3A to 3C, table 2.

EXAMPLE 4

Again using catalyst of the same composition as in example 1 and utilising a mixed chlorohydrocarbon feed, the effect of increasing the hydrogen chloride flow but at a higher temperature than example 2 is shown as example 4A to 4C, table 2.

EXAMPLE 5

Again using catalyst of the same composition as in example 1 and utilising a mixed chlorohydrocarbon feed, the effect of increasing the hydrogen chloride flow but at a higher temperature than example 2 and a lower oxygen flow is shown as example 5A to 5C, table 2.

Table 2 shows that under the three combinations of temperature and oxygen flow used, an increasing hydrogen chloride flow results in a decrease in the ethane burning rate. Furthermore, the efficiency with which ethane is converted within the reactor also increases as the hydrogen chloride flow to the reactor is increased.

TABLE 1

|  |  | EXAMPLE 1 | EXAMPLE 2 |
|---|---|---|---|
| CONDITIONS | TEMP. (°C.) - A | 480.7 | 477.5 |
|  | PRESS (BARG) | 0.1 | 0.1 |
| REACTANT | HCl | 48.0 | 66.0 |
| FLOWS IN | $C_2H_6$ | 37.5 | 37.5 |
| (LITERS PER | $N_2$ | 18.0 | 0.0 |
| HOUR) | $O_2$ | 42.0 | 43.2 |
| PRODUCT | $O_2$ | 2.9 | 2.9 |
| FLOWS OUT | CO | 0.9 | 1.4 |
| (LITERS PER | $CO_2$ | 4.6 | 3.5 |
| HOUR) | $C_2H_4$ | 5.0 | 4.5 |
|  | $C_2H_3Cl$ | 10.1 | 10.0 |
|  | $C_2H_5Cl$ | 4.7 | 4.8 |
|  | $C_2H_2Cl_2$ (A) | 3.3 | 4.4 |
|  | $C_2H_4Cl_2$ (B) | 0.6 | 0.7 |
|  | $C_2H_4Cl_2$ (C) | 3.4 | 3.3 |
|  | $C_2HCl_3$ | 0.3 | 0.3 |
|  | $C_2Cl_4$ | 2.0 | 2.4 |
|  | $C_2H_3Cl_3$ (D) | 0.2 | 0.1 |
|  | UNKNOWNS | 0.1 | 0.1 |
|  | $CHCl_3$ | 0.3 | 0.4 |
|  | $CCl_4$ | 0.9 | 1.1 |
| CONVERSION % | $O_2$ | 93.2 | 93.3 |
|  | $C_2H_6$ | 89.9 | 88.8 |
| YIELD ON | $C_2H_3Cl$ | 30.0 | 30.1 |
| ETHANE | $C_2H_5Cl$ | 13.8 | 14.4 |
| REACTED | $C_2H_4$ | 14.8 | 13.5 |
|  | $C_2H_2Cl_2$ (A) | 9.9 | 13.0 |
|  | $C_2H_3Cl_3$ (D) | 0.5 | 0.3 |
|  | $C_2HCl_3$ | 0.9 | 1.0 |
|  | $C_2Cl_3$ | 8.4 | 7.3 |
|  | $C_2H_4Cl_3$ | 12.0 | 11.7 |
|  | $CO + CO_2$ | 8.4 | 7.3 |
|  | CT (SEC) | 4.1 | 4.1 |
|  | SLV (CM/SEC) | 5.0 | 5.0 |

(NOTES: A—All 3 isomers, B—1,1 isomer, C—1,2 isomer, D—1,1,2 isomer)

TABLE 2

|  | EXAMPLE 3 | | | EXAMPLE 4 | | | EXAMPLE 5 | | |
|---|---|---|---|---|---|---|---|---|---|
|  | A | B | C | A | B | C | A | B | C |
| CONDITIONS | | | | | | | | | |
| TEMP (°C.) | 462 | 463 | 464 | 491 | 491 | 491 | 490 | 491 | 490 |
| PRESS/BARG) | 0.05 | 0.06 | 0.06 | 0.07 | 0.07 | 0.08 | 0.05 | 0.05 | 0.06 |
| REACTANT FLOWS IN | | | | | | | | | |
| (LITERS PER HOUR) | | | | | | | | | |
| $C_2H_5$ | 35.3 | 35.3 | 35.3 | 35.53 | 35.60 | 35.57 | 35.3 | 35.3 | 35.3 |
| HCl | 0 | 5 | 10 | 0 | 5 | 10 | 0 | 5 | 10 |
| $N_2$ | 59.2 | 59.1 | 59.1 | 59.6 | 59.6 | 59.6 | 59.9 | 59.9 | 59.9 |
| $C_2H_5Cl_2$ (C) | 47.6 | 47.6 | 47.6 | 37.5 | 37.5 | 37.5 | 40.0 | 40.0 | 40.0 |
| $C_2H_5Cl$ | 17.5 | 16.4 | 16.4 | 7.1 | 7.1 | 7.1 | 8.8 | 8.8 | 8.8 |
| $O_2$ | 37.8 | 37.8 | 37.8 | 38.2 | 38.2 | 38.2 | 28 | 28 | 28 |
| PRODUCT FLOWS OUT | | | | | | | | | |
| (LITERS PER HOUR) | | | | | | | | | |
| CO | 0.0 | 0.0 | 0.0 | 0.0 | 0.2 | 0.2 | 0.3 | 0.3 | 0.3 |
| $CO_2$ | 8.3 | 6.5 | 5.3 | 7.3 | 5.5 | 4.1 | 2.2 | 1.8 | 1.5 |
| $C_2H_5$ | 15.6 | 13.8 | 13.7 | 15.7 | 15.2 | 14.5 | 18.3 | 17.9 | 17.3 |
| $C_2H_5Cl$ | 18.6 | 19.6 | 21.1 | 24.3 | 26.3 | 27.8 | 25.9 | 26.7 | 26.9 |
| $C_2H_5Cl$ | 17.3 | 16.7 | 15.8 | 7.3 | 6.7 | 6.4 | 8.6 | 8.4 | 8.5 |
| $C_2H_5Cl_2$ (A) | 1.3 | 1.6 | 2.2 | 2.1 | 2.9 | 3.8 | 1.5 | 1.6 | 1.8 |

TABLE 2-continued

|  | EXAMPLE 3 | | | EXAMPLE 4 | | | EXAMPLE 5 | | |
| --- | --- | --- | --- | --- | --- | --- | --- | --- | --- |
|  | A | B | C | A | B | C | A | B | C |
| $C_2H_5Cl_2$ (B) | 0.6 | 0.7 | 0.7 | 0.4 | 0.4 | 0.4 | 0.4 | 0.4 | 0.4 |
| $C_2H_5Cl_2$ (C) | 31.6 | 32.5 | 32.2 | 17.0 | 16.5 | 16.3 | 19.5 | 19.2 | 19.2 |
| $C_2HCl_2$ | 0.1 | 0.1 | 0.1 | 0.2 | 0.3 | 0.3 | 0.3 | 0.3 | 0.2 |
| $C_2Cl_2$ | 0.2 | 0.2 | 0.1 | 0.5 | 0.0 | 0.3 | 0.3 | 0.3 | 0.2 |
| $C_2H_5Cl_2$ (D) | 1.6 | 2.3 | 2.9 | 1.2 | 1.6 | 1.3 | 0.9 | 0.9 | 0.6 |
| UNKNOWNS | 0.1 | 0.1 | 0.1 | 0.0 | 0.0 | 0.1 | 0.2 | 0.1 | 0.1 |
| $CHCl_2$ | 0.2 | 0.2 | 0.2 | 0.2 | 0.2 | 0.1 | 0.1 | 0.1 | 0.1 |
| $CCl_2$ | 0.3 | 0.4 | 0.4 | 0.3 | 0.3 | 0.2 | 0.2 | 0.2 | 0.2 |
| CONVERSIONS % | | | | | | | | | |
| $O_2$ | 89.9 | 91.7 | 92.7 | 96.2 | 96.9 | 95.7 | 98.7 | 98.9 | 98.4 |
| $C_2H_5$ | 66.8 | 70.3 | 73.3 | 82.9 | 85.6 | 86.6 | 76.7 | 77.4 | 78.8 |
| YIELD ON ETHANE REACTED | | | | | | | | | |
| $C_2H_5Cl$ | 78.8 | 78.9 | 81.4 | 82.4 | 86.4 | 90.4 | 95.5 | 97.8 | 96.8 |
| $CO + CO_2$ | 17.6 | 13.0 | 10.3 | 12.4 | 9.3 | 7.0 | 4.7 | 3.9 | 3.1 |
| $C_2H_5Cl_2$ (D) | 6.7 | 9.2 | 11.1 | 4.1 | 5.2 | 4.1 | 3.2 | 3.2 | 2.3 |
| $C_2HCl_2$ | 0.4 | 0.4 | 0.5 | 0.8 | 1.1 | 1.1 | 1.0 | 1.1 | 0.9 |
| $C_2Cl_2$ | 0.7 | 0.6 | 0.5 | 1.6 | 0.0 | 0.9 | 1.3 | 1.2 | 0.8 |
| CT SECS | 3.1 | 3.0 | 2.9 | 3.3 | 3.3 | 3.3 | 3.3 | 3.3 | 3.3 |
| SLV CM/S | 6.6 | 6.7 | 6.9 | 6.1 | 6.1 | 6.1 | 6.2 | 6.2 | 6.2 |

(NOTES:
A—All 3 isomers,
B—1,1 isomer,
C—1,2 isomer,
D—1,1,2 isomer)

We claim:

1. In a method for the production of vinyl chloride monomer by the catalytic oxychlorination of ethane which comprises causing reaction to occur in a reactor between ethane, an oxygen source and a chlorine source in the presence of a copper and alkali metal-containing catalyst and at a temperature of up to about 491° C., and thereafter recovering vinyl chloride monomer, the improvement comprising controlling the incidence of burning products by supplying HCl to the oxychlorination reaction in excess of the stoichiometric requirement for chlorine in the reaction and recycling HCl exhausted from the reactor to the reactor.

2. The method of claim 1 wherein the HCl is supplied together with an additional chlorine source.

3. The method of claim 1 or claim 2 wherein the ratio of excess HCl to ethane in the reaction is between 0.1 and 10.

4. The method of claim 3 wherein the ratio of excess HCl to ethane in the reaction is between 0.5 and 3.

* * * * *